United States Patent [19]

Timmons et al.

[11] Patent Number: 4,729,821

[45] Date of Patent: Mar. 8, 1988

[54] IN SITU ACTIVATION OF CATALYSTS BY APPLIED ELECTRICAL POTENTIALS

[75] Inventors: Richard B. Timmons, Arlington, Tex.; Sandor Kristyàn, Budapest, Hungary

[73] Assignee: Board of Regents, The University of Texas System, Austin, Tex.

[21] Appl. No.: 926,643

[22] Filed: Nov. 3, 1986

[51] Int. Cl.$^4$ .................. C07C 17/00; C07C 3/24
[52] U.S. Cl. .................. 204/164; 204/165; 204/168; 204/170; 502/5; 502/20; 502/514; 502/522
[58] Field of Search .............. 204/164, 165, 168, 170; 502/5, 20, 514, 522

[56] References Cited

U.S. PATENT DOCUMENTS

| | | | |
|---|---|---|---|
| 1,400,959 | 12/1921 | Koetschet | 204/170 |
| 3,953,305 | 4/1976 | Connolly | 204/97 |
| 3,977,901 | 8/1976 | Buzzelli | 136/86 A |
| 4,261,857 | 4/1981 | Nakao | 502/5 |
| 4,318,708 | 3/1982 | Högberg | 204/170 |
| 4,401,530 | 8/1983 | Clere | 204/98 |
| 4,499,025 | 2/1985 | Davison et al. | 204/59.7 |

FOREIGN PATENT DOCUMENTS 5253792 4/1970 Japan ........................... 502/5

OTHER PUBLICATIONS

Kristyan et al., Journal of Catalysis, vol. 101 (1986), pp. 331–341.

Primary Examiner—Arthur P. Demers
Attorney, Agent, or Firm—Arnold, White & Durkee

[57] ABSTRACT

A new method is described for the in situ activation of catalysts. Conductive catalysts or catalyst compositions are treated by applying a relatively high (up to 3,000 vdc), substantially electrostatic, potential to the catalyst while the surface of the catalyst is exposed to an ionizable gas. Activation is observed only when the catalyst is biased negatively with respect to a remote counter electrode. The activation persists even after the electrical potential is removed. This activation and, in some cases, catalyst regeneration is believed to arise from the production of cation radicals which react with and remove inactivating deposits on the catalytic surface. The process is demonstrated on the nickel-catalyzed hydrogenolysis of ehtane and ethylene.

18 Claims, 10 Drawing Figures

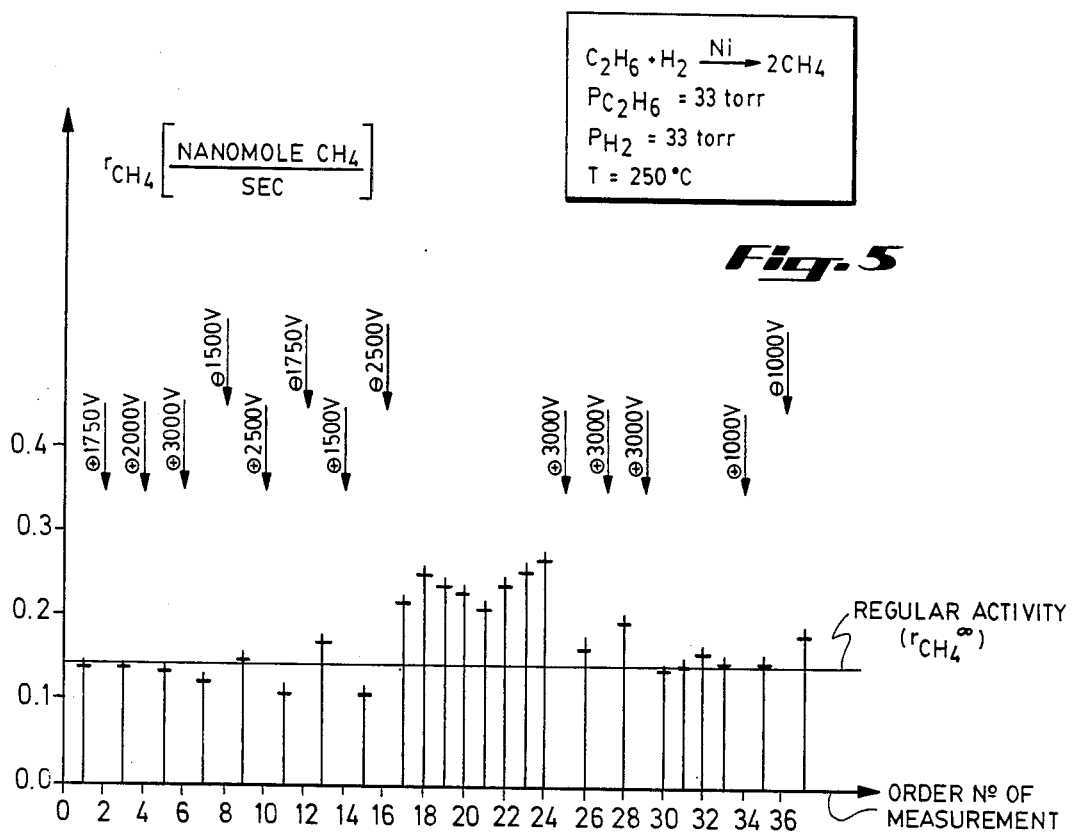
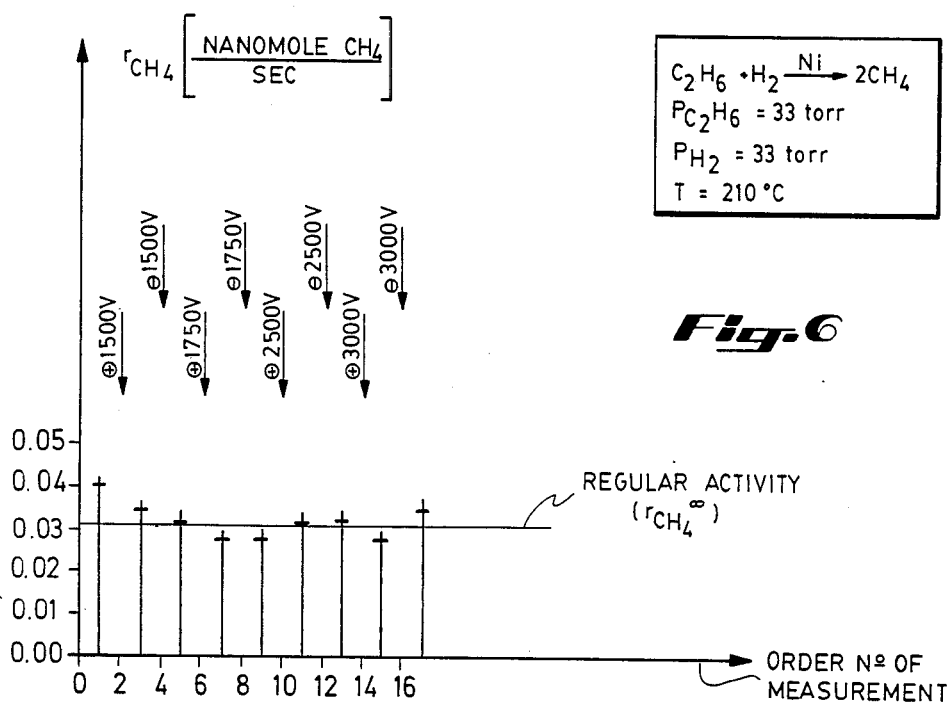

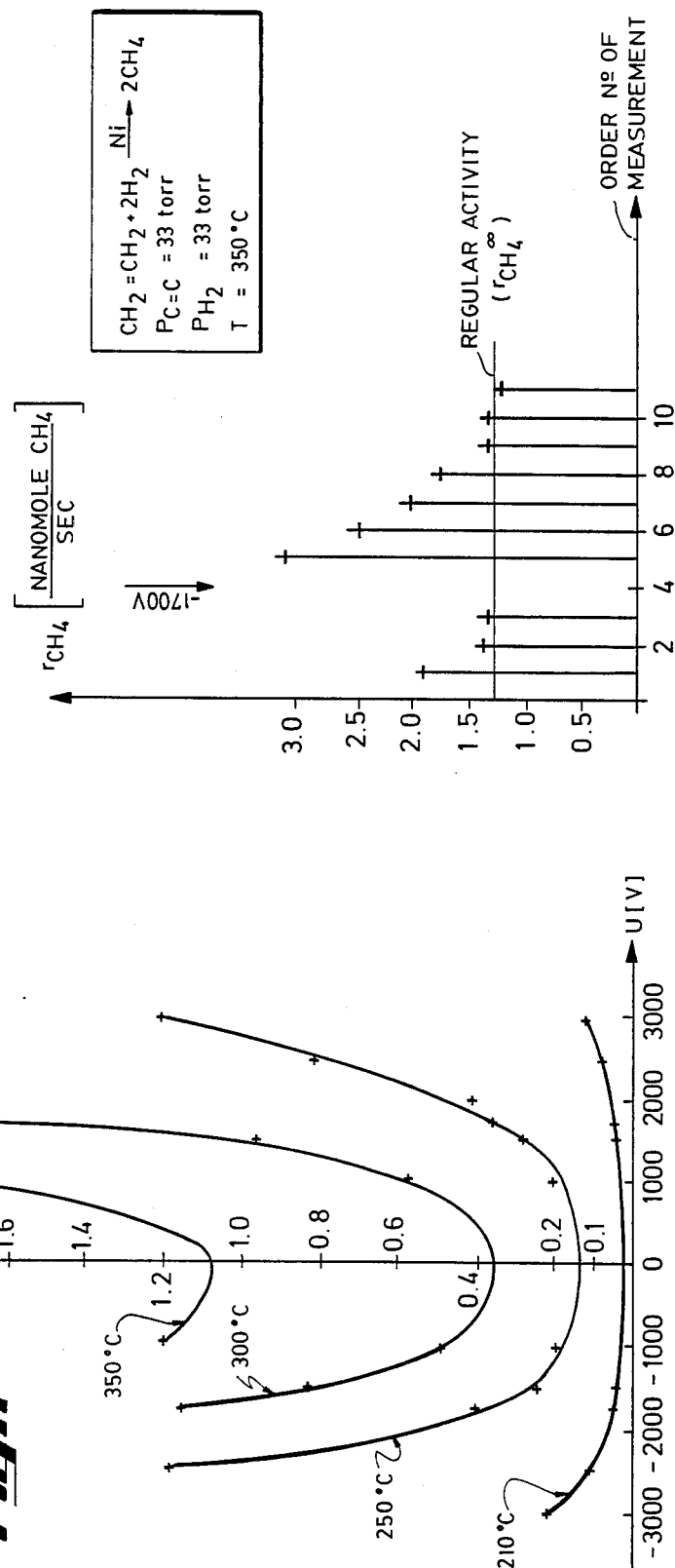
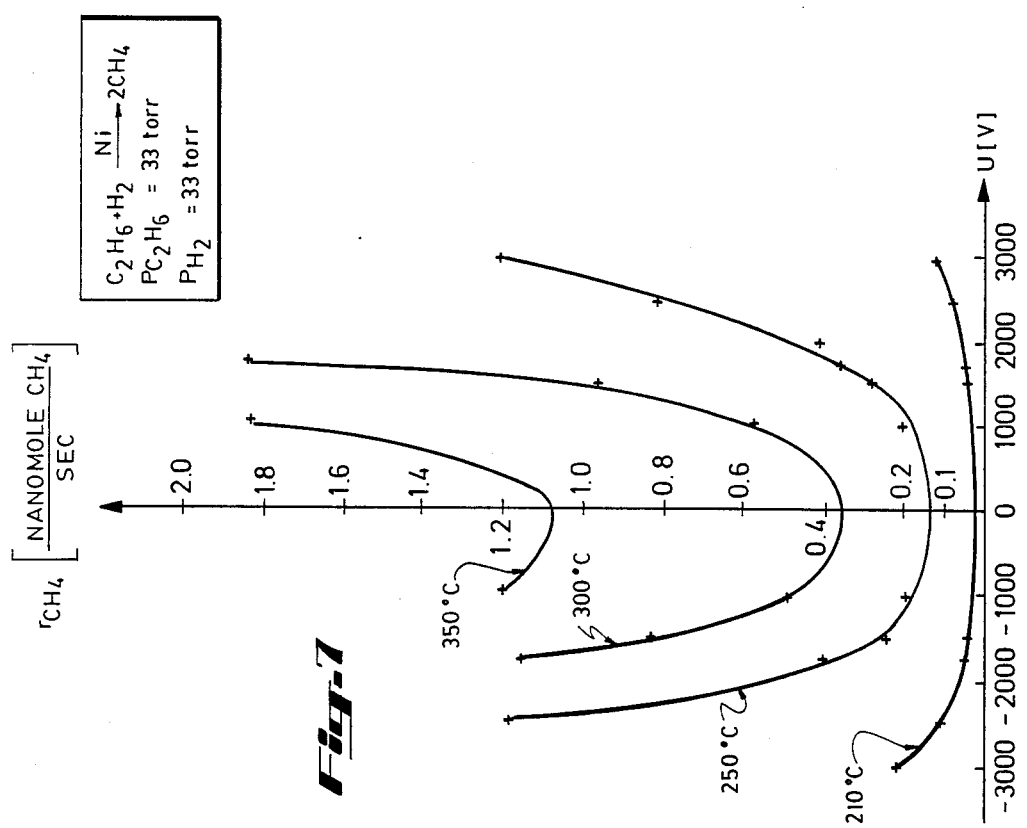
Fig. 7
Fig. 8

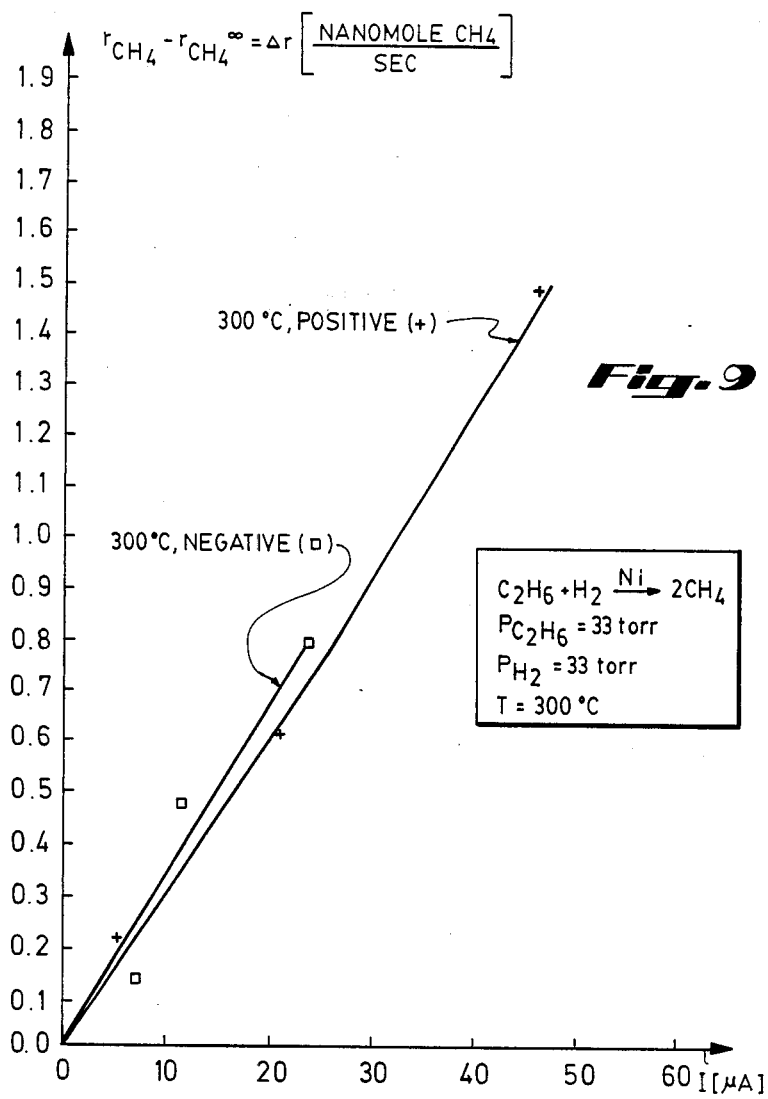
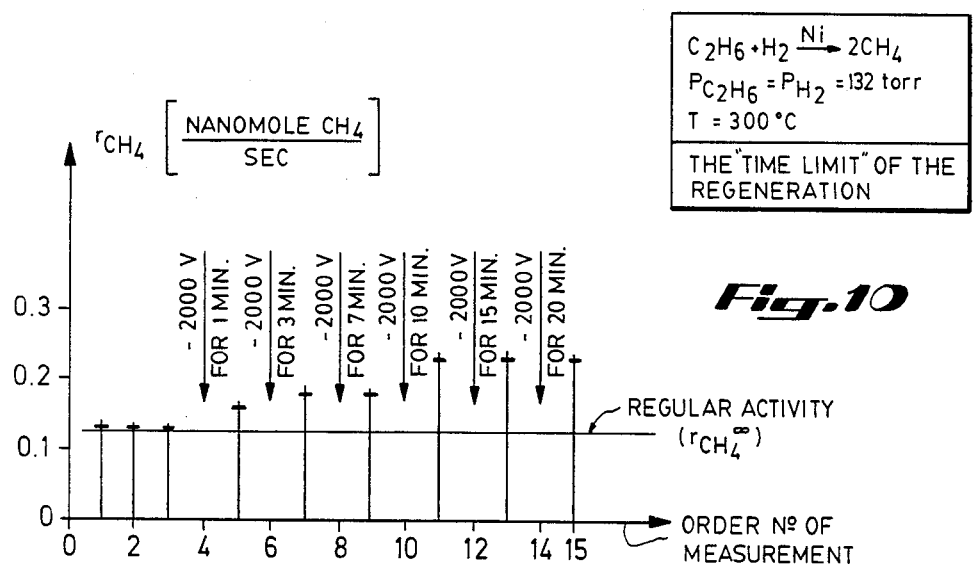

IN SITU ACTIVATION OF CATALYSTS BY APPLIED ELECTRICAL POTENTIALS

BACKGROUND OF THE INVENTION

1. Field of the Invention

This invention relates to catalysts. More specifically, it relates to solid-phase heterogeneous catalysts, especially metal surface catalysts used to enhance the rate of gas-phase reactions.

2. Description of the Problem

Catalysts are defined as substances which when added to a reaction mixture in less than stoichiometric quantities effect a change in the rate of the reaction. Catalysts are almost always employed to enhance the rate of reactions by lowering the energy of activation from that which prevails in the absence of a catalyst—i.e., the catalyst changes the mechanistic pathway. A catalyst affects the rate of a chemical reaction without itself being consumed or undergoing a chemical change. Thus, a catalyst can (theoretically) last indefinitely and/or be quantitatively recovered.

In practice, catalysts do not last indefinitely. The life of an industrial catalyst commonly varies from 1000 to 10,000 hours, after which it must be replaced or regenerated. This is especially true of solid-phase catalysts since the activity of a solid catalyst is often centered in a small fraction of its surface, and any decrease in the number of active points can significantly affect the activity of the catalyst. Substances which block or otherwise alter the catalytic surface in a way which decreases its activity are called "poisons." An oft-cited example of a catalyst poison is lead. Organic lead compounds (e.g., tetraethyllead, the antiknock compound used in some motor vehicle fuels) are known to virtually destroy the catalytic activity of emission control devices employing precious-metal catalysts such as platinum and palladium.

Of particular interest in the present context is a type of catalyst poisoning known as "coking." Coking occurs on the surface of a metal catalyst via the formation of metal-carbon bonds. This phenomenon has been observed in the nickel-catalyzed hydrogenolysis of $C_2H_6$ to $CH_4$. This particular reaction has been the subject of numerous kinetic studies. The reaction proceeds at a measurable rate at temperatures as low as 200° C. The observed rate increases rapidly as a function of temperature up to approximately 250° C.; and, less rapidly from about 250° to 350° C. Above 350° C. the reaction rate is relatively temperature independent. At temperatures between approximately 500° and 700° C. a decrease in the reaction rate is observed (relative to those measured at around 350° C.).

The temperature dependence of this reaction, including the slower reaction rates observed above about 500° C., has been the subject of numerous studies. These studies indicate that the decrease in the rate of the reaction at high temperatures is related to the formation of Ni—C bonds on the surface of the catalyst. This high temperature "coking" effects a poisoning of the catalyst with respect to the hydrogenolysis reaction. Indeed, recent surface studies have produced not only molecular confirmation of coking, but actual evidence of specific molecular structures for the surface-formed molecules. For example, cross-linking of initially formed unsaturated carbon chains which results in the eventual formation of a two dimensional graphite-like deposit is believed to be responsible for the high temperature inhibition of nickel catalysis in hydrogenolysis and dehydrogenolysis reactions. Other studies indicate that the formation of multiple metal-carbon atom bonds plays an important role in this inactivation process.

Regardless of the exact nature of the carbon-nickel molecular formations, the important fact from a practical standpoint is that those molecular interactions which lead ultimately to the deactivation of the nickel catalyst are significant at temperatures as low as 250° C. and become progressively more important with increasing temperatures. Regeneration of catalytic activity can be achieved with fair success at temperatures below about 250° C. by the use of hydrogen or steam treatments. At higher temperatures, the direct in situ regeneration of catalytic activity is much more difficult to achieve. It appears that the high temperature coking of the nickel catalyst results in the formation of metal carbide bonds and this process is virtually irreversible in terms of normal chemical regeneration techniques. It has been noted that treatment with oxygen can remove carbon formations at lower temperatures, but metal-oxide formation results at higher temperatures which decreases catalytic activity. Oxygen is apparently not successful in catalytic regeneration at temperatures above 360° C. where graphite formation is observed.

Nickel is used as a catalyst in many important industrial processes. For example, the steam-hydrocarbon reforming process:

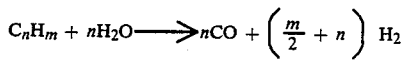

This reaction is commonly carried out on $C_1$ to $C_4$ hydrocarbons at high temperatures (760° to 980° C.) in the presence of a Ni catalyst. The products are usually subsequently subjected to a shift reaction at between 315° and 370° C. in order to maximize the production of hydrogen ($CO + H_2O \rightarrow CO_2 + H_2$). Poisoning of the nickel catalyst used in the reforming process is a serious economic problem.

Methanation reactions (e.g., $CO + 3H_2 \rightarrow CH_4 + H_2O$) are another example of nickel catalyzed reactions in which catalytic poisoning is a major problem. These reactions are commonly carried out at temperatures of about 315° C.

A major industrial use of Ni involves the hydrogenation of fats and oils. Hydrogenation is used to improve the keeping qualities, taste, and odor of such products. A typical example would be:

$$(C_{17}H_{31}COO)_3C_2H_5 + 3H_2 \rightarrow (C_{17}H_{33}COO)_3C_3H_5$$

The nickel catalyst employed in these hydrogenations is easily inactivated, especially by sulfur-containing compounds such as sulfur dioxide and hydrogen sulfide.

The catalytic cracking of ammonia is another important process which employs a nickel catalyst:

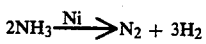

The reaction is carried out at 870° C. It is sometimes used for the on-site production of hydrogen inasmuch as ammonia is easier and less hazardous to transport than hydrogen. Again, the nickel catalyst is subject to poisoning.

A number of other metal catalysts used in industrially important processes are subject to poisoning and/or deactivation. Precious metals such as platinum, palladium, rhodium, ruthenium, osmium, and iridium are used in a wide variety of hydrogenations including the conversion of olefins to paraffins, dienes to monoenes, benzene to cyclohexane, alkynes to alkenes and/or paraffins, aldehydes to alcohols, nitro compounds to organo amines, resorcinols to dihydroresorcinols, ketones to alcohols, and cyanides to amines. In general, the catalysts employed are prone to deactivation via the deposition of surface inhibitors, particularly from sulfur-containing compounds.

The synthesis of ammonia from nitrogen employs an iron catalyst which contains a small quantity of mixed oxides:

$$N_2 + 3H_2 \rightarrow 2NH_3$$

The catalyst in this process is also subject to inactivation, especially at higher temperatures.

The 3-way catalytic converters used on automobiles in this country are another example of catalysts which suffer from surface deactivation by poisoning. These converters are used to oxidize carbon monoxide and unburned hydrocarbons and to reduce nitric oxide. Deposits on the catalytic surfaces, particularly those from lead and sulfur compounds, deactivate the catalysts and disable the converter.

SUMMARY OF THE INVENTION

Disclosed herein is a novel, inexpensive, and rapid method for the direct in situ activation of catalysts. The method is equally applicable to the regeneration of catalytic activity lost as a result of poisoning of the catalytic surface.

The method employs the creation of high electrostatic field gradients in the region near the surface of a solid phase catalyst. Enhanced reaction rates are observed when the reaction is allowed to proceed with the electrostatic field present. Even more unexpectedly, however, increased reaction rates are observed for a significant period of time after the electrostatic field is removed. Thus far, the catalytic activation which obtains even after the electric field is turned off has been observed only when the catalyst has been biased negatively with respect to a counter electrode which is separated from the catalyst by a dielectric. Since enhanced reaction rates are observed during periods when the catalyst is biased either positively and negatively, it is contemplated that the phenomenon of catalytic activation which persists after the imposition of a negative potential obtains as the result of a different mechanism.

BRIEF DESCRIPTION OF THE DRAWINGS

FIGS. 3, 4, 5, and 6 are bar graphs presenting reaction rate data versus run number for the hydrogenolysis of ethane at various temperatures, before and after the application of different electrical potentials to the catalyst.

FIG. 7 is a bar graph of the rate of methane production from the hydrogenolysis of ethane at various temperatures and applied voltages.

FIG. 8 is a bar graph of the rate of the catalytic hydrogenolysis of ethylene to methane at 350° C.

FIG. 9 shows in graph form the dependence of hydrogenolysis rate enhancement on current for reactions proceeding with voltage applied to the catalyst.

FIG. 10 illustrates the time dependence of the activation of the catalyst using an applied voltage of −2000 vdc.

DETAILED DESCRIPTION

The present invention can best be understood by reference to the following examples which constitute kinetic studies of the nickel-catalyzed, gas phase hydrogenolysis of ethane (reaction I, below) and of ethylene (reaction II, below).

$$C_2H_6 + H_2 \xrightarrow{Ni} 2CH_4 \qquad (I)$$

$$C_2H_4 + 2H_2 \xrightarrow{Ni} 2CH_4 \qquad (II)$$

EXAMPLE 1

Figure 1:
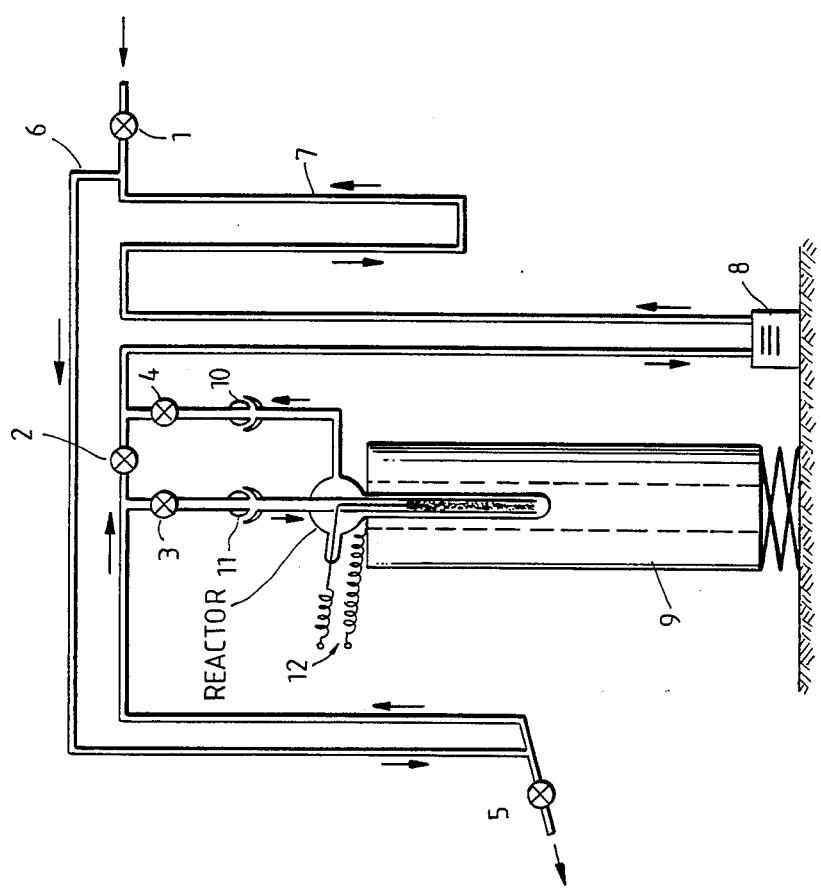
FIG. 1 depicts the gas-phase reaction system used to demonstrate the process of the present invention.

Reaction I (above) was carried out in a conventional glass reaction and gas handling system as shown in FIG. 1. Reactant gases were introduced into reaction loop 6 via stopcock 1. Stopcock 1 also provided a connection for a manometer to monitor the total pressure in the system. The gases were circulated through the system in the direction indicated by the arrows by means of mixer pump 8, a metal bellows type circulation pump.

The reactor (shown in more detail in FIG. 2) was surrounded by electric resistance heater 9. Both the inlet and outlet of the reactor were equipped with ground-glass ball joint connectors (11 and 10, respectively) for connection to gas circulation loop 6. U-tube 7 was provided in gas loop 6 for use in an optional cold trap. A cold trap, however, was not used in this or other experiments disclosed herein.

Gas loop 6 was also provided with sampling stopcock 5 for removing aliquots of the gas reaction mixture for analysis during the course of the experiment.

Figure 2:
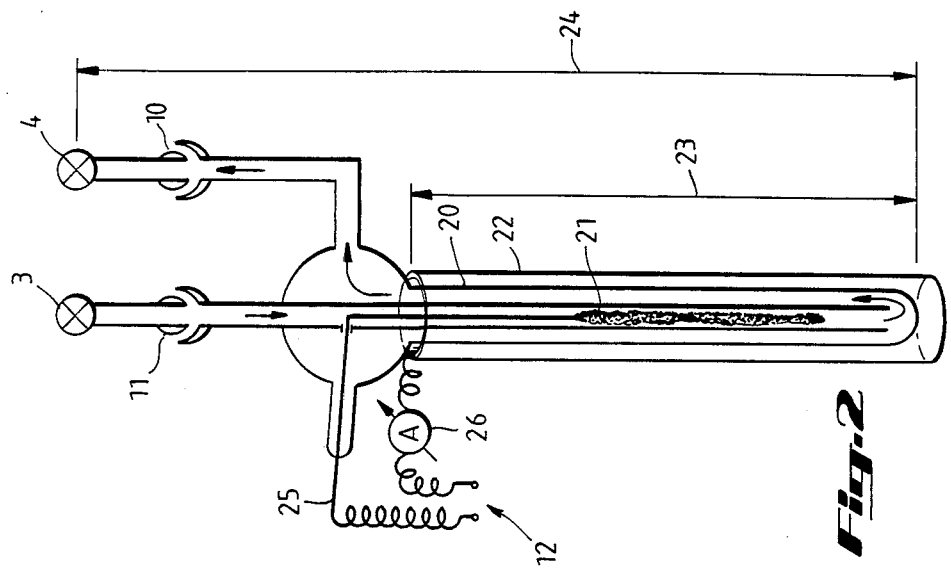
FIG. 2 schematically depicts the reactor section of the apparatus shown in FIG. 1.

Glass reactor 20 is shown in greater detail in FIG. 2. Nickel catalyst 21, comprising 50 meters of 0.127 mm diameter Ni wire coupled around catalyst support 25, was positioned on the center axis of the reactor. Catalyst support 25, comprising a length of heavier gauge Ni wire in electrical contact with nickel catalyst 21, was sealed in gas-tight relation to the wall of the reactor at the point where it passed through the wall. A length of catalyst support 25 projected beyond the wall of the reactor to provide electrical connection to the catalyst. The heated portion of the reactor is indicated by limits 23. Surrounding the heated portion of the reactor was counter electrode 22 which comprised an aluminum cylinder, 261 mm in length, 21.5 mm in diameter, and having a thickness of 0.7 mm. Electrical leads 12 were connected to both nickel wire 25 and counter electrode 22. Microammeter 26 was connected in series with electrical leads 12 and a high voltage power supply (Fluke, Model 415B).

The reactor was connected to the gas loop of the circulation system by means of ball joints 11 and 12 on the inlet and outlet, respectively. The total internal volume of the reactor within indicated limits 24 was 172.6 cubic centimeters.

Prior to each kinetic run, the nickel wire catalyst was treated by exposure to hydrogen gas at a pressure of 33 torr for 20 minutes to produce a standard catalytic surface. This treatment was performed at a temperature of 300° C. The system was then evacuated, stopcocks 3 and 4 were closed, stopcock 2 was opened, and gas loop 6 was charged with 33 torr each of ethane and hydrogen. Mixer pump 8 was operated for a period of five minutes to mix the reactant gases. After mixing, the reaction was initiated by the simultaneous opening of stopcocks 3 and 4. Stopcock 2 was then closed so that the circulation of gases would be around gas loop 6 and through the reactor as shown by the arrows in FIGS. 1 and 2. Gas circulation was maintained by operation of mixer pump 8 throughout the kinetic runs.

Heater 9 was used to maintain a temperature of 300° C. in the heated portion of the reactor during each kinetic run. The rate of product formation was monitored by periodically taking an aliquot of the reaction mixture via sampling port 5 and expanding it into the evacuated sample loop of a direct injection gas sampling valve on a gas chromatograph. The analysis of methane produced by the hydrogenolysis reaction was performed by gas-liquid chromatography using a column with a squalane stationary phase and flame ionization detection.

Figure 3:
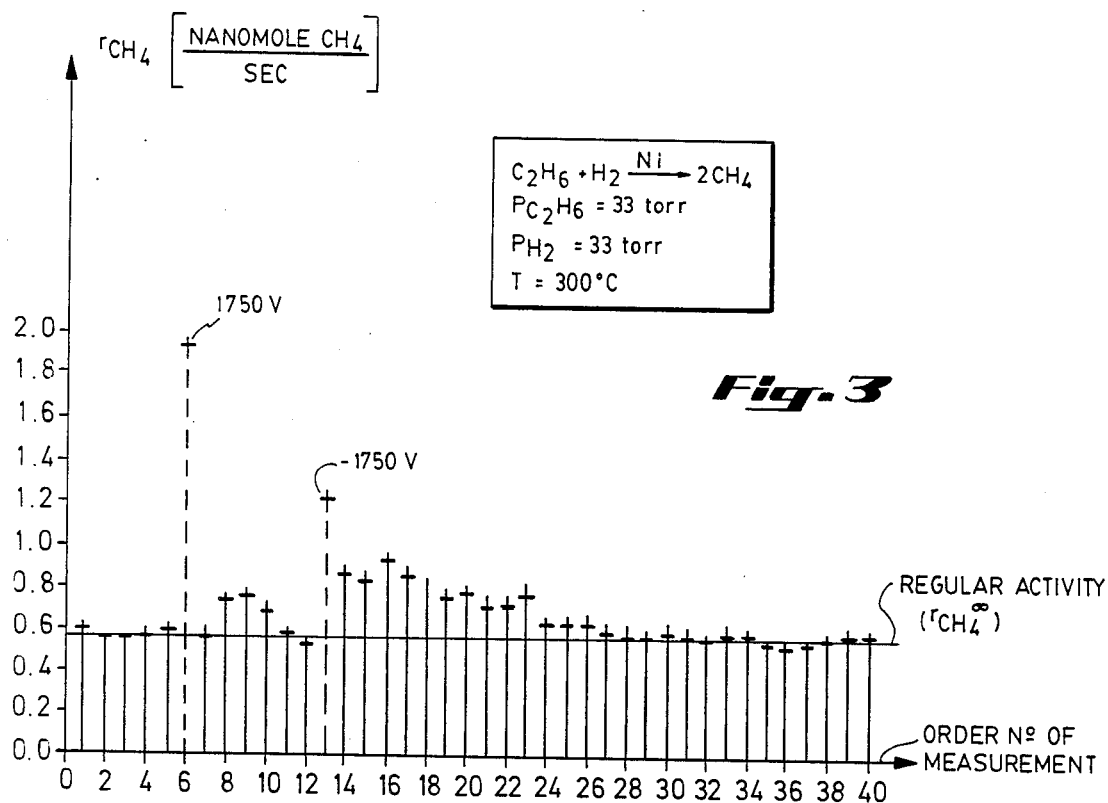

Kinetic data obtained from 40 consecutive runs is presented in bar graph form in FIG. 3. The rate of the hydrogenolysis reaction, measured in terms of nanomoles of methane produced per second, is plotted versus the sequential order number ("run number") of the experiment. The first 5 runs were obtained with zero potential difference between the nickel wire catalyst and the aluminum cylinder counter electrode to establish the "normal" catalytic reaction rate. The runs were each of 20 minutes duration. In general, the rate of methane formation was reproducible within ±10%. This base rate, calculated by computing the average of the first five runs, and representing the regular activity of the nickel catalyst is shown as a horizontal line at about the 0.56 nanomole/sec level on the ordinate axis.

During run #6, a positive potential of 1750 vdc was imposed on the nickel wire catalyst via electrical leads 12. The observed rate of methane formation during this run was more than triple that previously measured (runs 1–5). Kinetic runs at zero potential difference performed immediately subsequent to the application of the positive potential (runs 7–12) showed no consistent rate enhancement.

During run #13, a negative potential of 1750 vdc was imposed on the nickel wire catalyst. The observed rate of methane formation during this run was more than double the "regular activity." Most unexpectedly, however, enhanced rates of hydrogenolysis were observed during kinetic runs at zero potential difference performed subsequent to the run in which the catalyst was negatively charged. This enhancement decayed back to the "regular activity" level over the course of about fourteen 20-minute runs (runs 14–27). Consistent catalytic activity at the base rate was observed thereafter (runs 28–40).

It bears repeating that the potentials applied to the catalyst, both positive and negative, were imposed during an otherwise normal kinetic run. Thus, throughout the periods of voltage application, the catalyst was exposed to both hydrogen and ethane, as well as any methane formed via the hydrogenolysis reaction. It is also important to note that treatment of the Ni wire with 33 torr $H_2$ was carried out between all successive runs, including runs immediately following the application of voltages to the electrodes.

Currents in the range of 10 to 50 microamps were observed in the course of the runs in which voltage potentials were applied. For a given applied potential, the current observed was a sensitive function of both reactant gas pressure and reactor temperature, decreasing with increased pressure and increasing with increased temperature. It is believed that the temperature dependence of the current observed includes contributions from both the gas and reactor wall conductivity changes. For a given pressure and temperature, the current increased slowly with increasing applied voltage up to the point at which electrical breakdown of the dielectrics separating the two electrodes occurred. This breakdown was manifest as a sudden current surge with concomitant visible arcing between the nickel wire and the aluminum cylinder surrounding the reactor.

EXAMPLE 2

Figure 4:
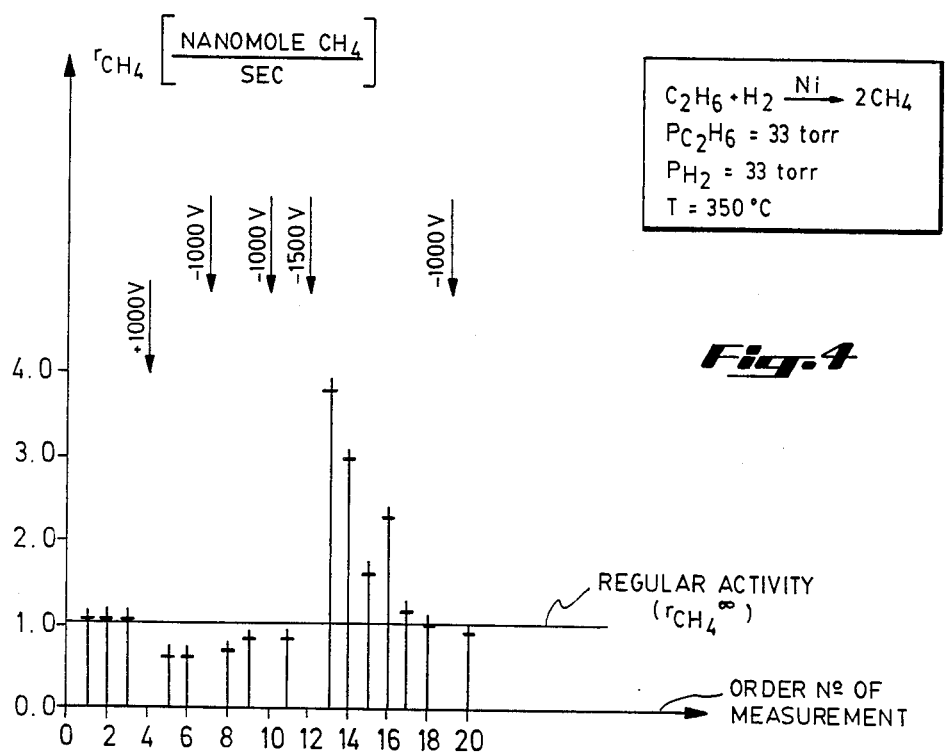

Kinetic runs were performed as in Example 1, but the temperature of the reactor was maintained at 350° C. Three runs at zero applied potential were made to establish "regular activity" of the nickel wire catalyst. The results of the rate measurements are shown in FIG. 4, runs 1–3 being those used to establish the base rate. During run 4 a potential of +1000 vdc was continuously applied to the catalyst. Rates obtained during runs with voltage potentials applied to the catalyst are not shown in FIG. 4, but may be found in FIG. 7.

Runs performed at zero applied potential subsequent to run 4 exhibited a decrease in catalytic activity (runs 5 and 6), as did those following runs wherein the catalyst was biased at a negative 1000 vdc relative to the aluminum cylinder (runs 8, 9, and 11). However, five runs subsequent to one during which a negative 1500 vdc were applied to the catalyst each exhibited a rate enhancement (runs 13–17). The decay in catalytic activity back to the base rate obtained in fewer runs than in the series of runs performed at 300° C.

During run 19 the catalyst was again biased at a negative 1000 vdc relative to the aluminum cylinder surrounding the reactor. No increase in catalytic activity was observed during the run at zero applied potential which immediately followed that run.

EXAMPLE 3

Kinetic runs were performed as in Example 1, but with the temperature of the reactor maintained at 250° C. Measured hydrogenolysis reaction rates are shown in FIG. 5. Rate data for runs during which various potentials were applied to the metal catalyst are omitted, but may be found in FIG. 7.

The results of this series of experiments may be read directly from FIG. 5. Most noteworthy is the fact that no consistent post-voltage-application rate enhancement obtained other than in runs 17–24, which followed a run wherein a negative potential of 2500 vdc was applied to the catalyst. Moreover, in that particular group of kinetic runs there is no apparent decay of the rate back towards the base level.

EXAMPLE 4

Kinetic runs were performed as in Example 1, but with the temperature of the reactor maintained at 210° C. Measured hydrogenolysis reaction rates are shown in FIG. 6. Rate data for runs during which various potentials were applied to the metal catalyst are omitted, but may be found in FIG. 7.

At this temperature, applications of potential differences as high as 3000 vdc had no apparent effect on increasing catalytic activity in runs carried out immediately after those during which such potentials were applied.

EXAMPLE 5

A series of kinetic experiments on the nickel-catalyzed hydrogenolysis of ethylene (reaction II, above) was performed under conditions similar to those used in the experiments of Example 2, ethylene gas being substituted for ethane. Rate data for a number of kinetic runs is presented in FIG. 8.

Significant post-voltage-application rate enhancement was found in four runs performed after a hydrogenolysis was accomplished while the catalyst was biased at a negative 1700 vdc relative to the aluminum cylinder. It is interesting to note that the rate of decay of catalytic activity in runs 5–9 is very similar to that observed in the hydrogenolysis of ethane performed at the same temperature (see FIG. 4, runs 13–17). This suggests that the same mechanism may be responsible in both reactions for the decay in enhanced catalytic activity.

EXAMPLE 6

In view of the apparent improved catalytic activity which obtained immediately following runs wherein certain minimum negative potentials were applied to the catalyst, a series of experiments was performed to determine whether the phenomenon was time-dependent. The results of these experiments, carried out at 300° C. and 264 torr total pressure, are shown in FIG. 10. After establishing the baseline regular activity of the catalyst in the first three runs, a series of kinetic runs were conducted which involved the application of a negative 2000 vdc to the catalyst for the indicated interval of time. Immediately following each of these runs, a run was performed at zero applied potential and the rate of methane formation measured. These rates are plotted in FIG. 10.

It appears that under these particular experimental conditions, approximately 10 minutes are required to achieve the full extent of catalytic activation. Stated another way—runs of less than 10 minutes duration with a voltage potential applied to the catalyst did not produce as great a degree of activation of the catalyst as did runs for periods of 10 minutes or more.

EXAMPLE 7

As noted above, rate data for the hydrogenolysis of ethane at various temperatures and applied potentials may be found in FIG. 7. It was not possible to extend the experiment to higher voltages at the higher temperatures inasmuch as the breakdown voltage decreased rapidly with increasing temperature.

The approximate symmetry of FIG. 7 about the y-axis suggests that the phenomenon is independent of the polarity of the catalyst. Unlike the post-voltage-application rate enhancement which seems to obtain only after the catalyst has been biased negatively with respect to the counter electrode, this phenomenon is observed with the catalyst biased both positively and negatively, which implies that a different mechanism is responsible for this rate enhancement.

Although not wishing to be held to any particular theory, it is contemplated that the increased rates of methane formation during the runs wherein a potential was applied to the catalyst arise from current-induced ion molecule reactions and do not represent an increase in the activity of the catalyst per se. Using the same data as that shown in FIG. 7 for runs at 300° C., differences in the rate of methane formation were calculated (rate with potential applied minus rate at zero potential). Each difference was then plotted versus the current measured during the run with the potential applied to the catalyst. FIG. 9 depicts these plots for both positive and negative potentials. The rough linearity of these plots is further evidence that the enhanced rate of methane formation during runs carried out with a potential applied to the catalyst simply results from the inducement of gas phase ion-molecule reactions some of which lead to methane formation. Similar plots with approximately the same slopes, were obtained using data from kinetic runs over the temperature range 210° to 350° C.

In view of the very low power consumed in these experiments it does not seem that the acceleration in reaction rate during runs with applied potentials could arise from resistance heating of the nickel wire catalyst. For example, the current observed with an applied potential of 2000 vdc at 250° C. was less than 20 microamps. The resistance of the Ni wire was less than 800 ohms. Therefore, the power dissipated by the Ni wire was less than $3 \times 10^{-7}$ watts. Over the course of a 20-minute kinetic run, this represents an energy consumption of $4 \times 10^{-4}$ joules. Since the heat capacity of the 5-gram nickel catalyst was approximately 3 J/K, this would produce a maximum temperature rise of less than 0.0001° C.

Although the invention disclosed herein does not depend upon any explanation of the reason why catalyst activation results from the practice of the process, it is interesting to contemplate the possible mechanisms which may be involved.

Under no reaction conditions investigated were consistent increases in rate observed following runs with positive potentials applied to the Ni wire catalyst. The extent of the rate increase observed following application of negative potentials was strongly dependent on the temperature of the reaction, both in terms of the magnitude of the effect and its persistence as observed in runs at zero applied potential carried out subsequent to the treatment run. It seems reasonable to conclude that during runs in which a voltage potential was applied (and a current flow resulted), surface processes on the catalyst occurred. Presumably, these surface reactions produced a net increase in the number and/or nature of active sites present on the nickel surface. For example, a diminution of carbon deposits or metal-carbon bonding (i.e., "coking") would be expected to effect an increase in the activity of the catalyst. In this regard, it is important to note two experimental facts associated with these observations. First, the effect is only observed when the nickel wire catalyst is negatively biased to a relatively high potential (current in excess of 20 microamps). Secondly, as shown in FIG. 10, there is a time dependence associated with the creation of the enhanced reactivity. Thus the activation of the surface might be associated with direct electron emission or possibly reactions involving gas phase cations with carbon on the surface of the catalyst. The latter possibility could conceivably result from high-energy collisions of the cations generated with the electron-rich surface carbon species. By charge transfer, this could lead to removal of the surface carbon atoms. Along these lines, it should be noted that the application of a negative potential to the Ni wire under conditions in which the cell was evacuated (P<10$^{-3}$ torr), and relatively small leakage currents were observed, produced essentially no enhancement of reaction rate in subsequent runs at zero potential. This observation lends credence to the postulated cation activation mechanism.

Regardless of the exact mechanism, it is clear that surface activation of the Ni wire catalyst was achieved under conditions which normally produce deactivation—i.e., high temperature reactions in which carbide formation would be expected to occur. The observed rapid decrease in the activation with increasing temperature presumably represents the reestablishment of carbon surface deposits—a known high temperature phenomenon. It is important to note that in connection with the apparent lack of activation observed at lower applied potentials (e.g., −1000 vdc at 350° C.), the normal catalyzed hydrogenolysis reaction was proceeding and this likely involved continuous deposition of carbon on the surface of the nickel catalyst. At lower potentials (and currents), the rate of the activating effect may be insufficient to overcome completely the rate of carbon deposition. Apparently, as the current (and/or voltage) increases, a condition is eventually attained in which a net decrease in carbon surface deposition obtains.

The results of the experiments at 210° and 250° C. are particularly interesting in light of the above discussion. Previous kinetic studies of these nickel catalyzed hydrogenolysis reactions have shown that catalytic poisoning below 250° C. is a relatively slow process. For example, the generation of an activated catalyst at 250° C. by the application of a negative 3000 vdc potential to the Ni wire produced an increase in the activity of the catalyst which was essentially maintained without change during the course of eight subsequent runs representing close to 3 hours of catalysis. The fact that no enhanced activity was observed at 210° C. presumably indicates that when the reaction is commenced with a clean surface, no significant carbon deposition occurs and hence no restoration of activity can be had. Alternatively, it may be that the mechanism responsible for the activation is itself temperature dependent and thus a certain temperature must be achieved in order to surmount an activation energy barrier.

While the process of the invention has been described in connection with a metal catalyst, it is expected that the process can also be used to enhance the activity of nonmetal catalysts and/or catalysts which are nonconductors (e.g., zeolites). One way of accomplishing this would be to employ an electrically conductive catalyst composition comprising a normally non-conductive catalyst supported by an electrical conductor or conductive surface. The potential difference would then be imposed between the conductive support of the catalyst composition and a remote counter electrode.

Although developed in the context of a gas phase reaction, the invention could be practiced to increase the activity of conductive catalysts or catalyst compositions used for the heterogeneous catalysis of liquid phase reactions. In such a case the catalyst or catalyst composition could be removed or separated from the liquid reactant(s) and/or product(s) and then exposed to an atmosphere comprising an ionizable gas. A negative electrical potential would then be imposed as disclosed above to activate the catalyst.

It is expected that a wide variety of ionizable gases would be effective in the practice of this invention with those producing carbon atom radicals upon ionization being particularly preferred. It is believed that an important property of the gas chosen is its ability to produce reactive species under the influence of an electric field.

Normally, the gas will be employed at a pressure less than atmospheric, the range 30 to 100 torr being preferred. The optimum temperature for the process will depend on the particular gas chosen and the nature of the inactivating deposits (if any) on the surface of the catalyst. Although not wishing to be held to any particular theory, it is expected that if the mechanism of the process is one which involves the reaction of an inactivating surface deposit with ionized reactive gas species, an effective temperature for the process would be one which was sufficient to volatilize the product of such a reaction from the surface of the catalyst.

While presently preferred embodiments have been shown and described with particularity, the invention may otherwise be embodied within the scope of the appended claims. Various changes or modifications coming within the spirit of our invention may suggest themselves to those skilled in the art. Hence, the invention is not to be limited to the specific form of the process described or uses mentioned.

What is claimed is:

1. A process for increasing the rate of a catalyzed gas phase reaction wherein a gas phase reactant is reacted in the presence of an electrically conductive catalyst to form a desired product which comprises applying a negative electrical potential to the catalyst composition in the presence of the reactant at a potential difference and for a time sufficient to increase the rate of the product forming reaction and to maintain an increased rate of product formation after the potential difference is removed.

2. A process as recited in claim 1 wherein the electrical potential applied is less than that which produces arcing.

3. A process as recited in claim 1 wherein the reactant is a hydrocarbon.

4. A process as recited in claim 1 wherein the reactant is hydrogen.

5. A process as recited in claim 1 wherein the reactant is ethane.

6. A process as recited in claim 1 wherein the reactant is ethylene.

7. A process as recited in claim 1 wherein the gas phase reaction is the nickel-catalyzed hydrogenolysis of ethane.

8. A process as recited in claim 1 wherein the gas phase reaction is the nickel-catalyzed hydrogenolysis of ethylene.

9. A process for increasing the rate of a catalytic gas phase reaction wherein gas phase reactants are reacted in the presence of an electrically conductive catalyst composition to form a desired product which comprises applying a non-arcing negative electrical potential to the catalyst in the presence of the reactants at a potential difference and for a time sufficient to increase the rate of the product forming reaction and to maintain an increased rate of product formation after the potential difference is removed.

10. A process as recited in claim 9 wherein at least one of the reactants is a hydrocarbon.

11. A process as recited in claim 9 wherein at least one of the reactants is hydrogen.

12. A process as recited in claim 9 wherein the reactants are ethylene and hydrogen.

13. A process as recited in claim 9 wherein the reactants are ethane and hydrogen.

14. A process for activating an electrically conductive catalyst composition which comprises applying a non-arcing negative electrical potential to the catalyst composition while the catalyst composition is exposed to at least one gas selected from the group consisting of hydrocarbons and hydrogen.

15. An activated electrically conductive catalyst composition produced by applying a non-arcing negative electrical potential to the catalyst composition while the catalyst composition is exposed to at least one gas selected from the group consisting of hydrocarbons and hydrogen.

16. A process for activating an electrically conductive catalyst used to catalyze a liquid phase reaction which comprises applying a negative electrical potential to the catalyst while exposing the catalyst to a gaseous atmosphere comprising an ionizable gas of a type, at a potential, and for a time sufficient to increase the catalytic activity of the catalyst in the liquid phase reaction.

17. A process for activating an electrically conductive catalyst composition used to catalyze a liquid phase reaction which comprises applying a negative electrical potential to the catalyst composition while exposing the catalyst composition to a gaseous atmosphere comprising an ionizable gas of a type, at a potential, and for a time sufficient to increase the catalytic activity of the catalyst composition in the liquid phase reaction.

18. An activated electrically conductive catalyst produced by applying a negative electrical potential to the catalyst while exposing the catalyst to a gaseous atmosphere comprising an ionizable gas of a type, at a potential, and for a time sufficient to increase the catalytic activity of the catalyst.

* * * * *

UNITED STATES PATENT AND TRADEMARK OFFICE
CERTIFICATE OF CORRECTION

PATENT NO. : 4,729,821

DATED : March 8, 1988

INVENTOR(S) : Richard B. Timmons et al.

It is certified that error appears in the above-identified patent and that said Letters Patent is hereby corrected as shown below:

In the Abstract, last line, "ehtane" should be -- ethane --.

Column 4, line 46, "coupled" should be -- coiled --.

Signed and Sealed this

Twelfth Day of July, 1988

Attest:

DONALD J. QUIGG

*Attesting Officer*       *Commissioner of Patents and Trademarks*